United States Patent [19]
Wellinghoff et al.

[11] Patent Number: 5,922,776
[45] Date of Patent: Jul. 13, 1999

[54] SUSTAINED RELEASE, TRANSPARENT BIOCIDAL COMPOSITIONS

[75] Inventors: Stephen T. Wellinghoff; Joel J. Kampa, both of San Antonio, Tex.; Sumner A. Barenberg; Peter N. Gray, both of Chicago, Ill.

[73] Assignee: Bernard Technologies, Inc., Chicago, Ill.

[21] Appl. No.: 08/651,876

[22] Filed: Jun. 4, 1996

Related U.S. Application Data

[60] Provisional application No. 60/000,144, Jun. 12, 1995.
[51] Int. Cl.$^6$ .......................... A61K 47/30; A01N 25/08; A01N 25/34
[52] U.S. Cl. ........................ 514/772.3; 106/15.05; 252/187.23; 424/405; 424/408; 424/409; 424/410; 424/412
[58] Field of Search .............................. 252/187.1, 187.2, 252/187.23, 187.21; 514/772.3; 424/405, 408, 409, 410, 412; 106/15.05

[56] References Cited

U.S. PATENT DOCUMENTS

| | | | |
|---|---|---|---|
| 2,071,625 | 2/1937 | Haas et al. | 99/172 |
| 2,482,891 | 9/1949 | Aston | 252/187 |
| 2,546,568 | 3/1951 | Taylor | 99/150 |
| 2,558,942 | 7/1951 | Eagleson | 167/30 |
| 3,183,057 | 5/1965 | Marks et al. | 21/58 |
| 3,585,147 | 6/1971 | Gordon | 252/187 |
| 3,591,515 | 7/1971 | Lovely | 252/187 |
| 3,767,787 | 10/1973 | Segal | 424/76 |
| 4,104,190 | 8/1978 | Hartshorn | 252/187 R |
| 4,330,531 | 5/1982 | Alliger | 424/149 |
| 4,499,077 | 2/1985 | Stockel et al. | 424/149 |
| 4,504,442 | 3/1985 | Rosenblatt et al. | 422/37 |
| 4,547,381 | 10/1985 | Mason et al. | 426/316 |
| 4,585,482 | 4/1986 | Tice et al. | 106/15.05 |
| 4,681,739 | 7/1987 | Rosenblatt et al. | 422/37 |
| 4,689,169 | 8/1987 | Mason et al. | 252/186.24 |
| 4,728,498 | 3/1988 | Theeuwes | 422/29 |
| 4,748,904 | 6/1988 | Razeto et al. | 99/467 |
| 4,829,129 | 5/1989 | Kelley | 525/326.9 |
| 4,880,638 | 11/1989 | Gordon | 424/662 |
| 4,889,654 | 12/1989 | Mason et al. | 252/100 |
| 4,891,216 | 1/1990 | Kross et al. | 424/78 |
| 4,925,645 | 5/1990 | Mason | 423/477 |
| 4,956,184 | 9/1990 | Kross | 424/661 |
| 4,975,109 | 12/1990 | Friedman et al. | 71/67 |
| 4,986,990 | 1/1991 | Davidson et al. | 424/665 |
| 5,126,070 | 6/1992 | Leifheit et al. | 252/186.36 |
| 5,252,343 | 10/1993 | Kross | 424/661 |
| 5,306,440 | 4/1994 | Ripley et al. | 252/186.33 |

(List continued on next page.)

FOREIGN PATENT DOCUMENTS

| | | |
|---|---|---|
| 0 287 074 | 4/1988 | European Pat. Off. . |
| 0 611 162 | 2/1994 | European Pat. Off. . |
| 0 611 163 | 2/1994 | European Pat. Off. . |
| 57/198775 | 12/1982 | Japan . |
| 60/092759 | 5/1985 | Japan . |
| 4/164005 | 6/1992 | Japan . |
| 6/107971 | 4/1994 | Japan . |
| 2151138 | 12/1984 | United Kingdom . |
| 85/04107 | 9/1985 | WIPO . |
| 88/09176 | 5/1988 | WIPO . |
| 96/18300 | 6/1996 | WIPO . |

OTHER PUBLICATIONS

"Keeping Food Fresh Longer" Southwest Research Institute brochure, San Antonio, TX (reprinted from Technology Today) Jun. 1995, 4 pages.

*Primary Examiner*—Ponnathapura Achutamurthy
*Attorney, Agent, or Firm*—Senniger, Powers, Leavitt & Roedel

[57] ABSTRACT

A composition for retarding bacterial, fungal and viral contamination and mold growth containing an acid releasing polymer, a hydrophilic material, and chlorite anions. Each component of the composition has a particle size of not more than about 1,000 angstroms. The composition is substantially free of water and capable of releasing chlorine dioxide upon hydrolysis of the acid releasing polymer.

59 Claims, 1 Drawing Sheet

U.S. PATENT DOCUMENTS

| | | | |
|---|---|---|---|
| 5,360,609 | 11/1994 | Wellinghoff | 514/772.3 |
| 5,384,134 | 1/1995 | Kross et al. | 424/661 |
| 5,387,350 | 2/1995 | Mason | 210/754 |
| 5,399,288 | 3/1995 | Marzouk et al. | 252/186.21 |
| 5,405,549 | 4/1995 | Pitochelli | 252/187.21 |
| 5,631,300 | 5/1997 | Wellinghoff | 514/772.3 |
| 5,639,295 | 6/1997 | Wellinghoff et al. | 106/15.05 |
| 5,650,446 | 7/1997 | Wellinghoff et al. | 514/772.3 |
| 5,668,185 | 9/1997 | Wellinghoff | 514/772.3 |
| 5,705,092 | 1/1998 | Wellinghoff et al. | 252/187.21 |
| 5,707,739 | 1/1998 | Wellinghoff et al. | 428/403 |

SUSTAINED RELEASE, TRANSPARENT BIOCIDAL COMPOSITIONS

REFERENCE TO RELATED APPLICATIONS

This application is a continuation-in-part application of provisional U.S. Ser. No. 60/000,144 filed Jun. 12, 1995.

BACKGROUND OF THE INVENTION

The present invention relates generally to an optically transparent or translucent biocidal composition that releases chlorine dioxide upon being activated, and methods of using the composition.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

Chlorine dioxide or sodium chlorite have also been incorporated in food packaging. Studies have shown that residual levels of such preservatives do not result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an EPA study of the reaction of chlorine dioxide with water borne organics confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels that generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al. U.S. Pat. No. 4,585,482 describes gradual hydrolysis of alternating poly(vinyl methyl ether-maleic anhydride) or poly(lactic-glycolic acid) to generate acid that can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule to retain water within the capsule. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

Wellinghoff et al. have formulated composites that include a hydrophobic phase containing an acid releasing agent and a hydrophilic phase containing chlorite anions. The composite is substantially free of water until it is exposed to moisture. Once exposed to moisture, acid and hydronium ions are generated in the hydrophobic phase. The hydronium ions migrate to the hydrophilic phase and react with chlorite anions to release chlorine dioxide from the composite. These composites are composed of and generate only FDA approved substances or substances generally recognized as safe. The composites can be used for food packaging and other applications where the substances can be ingested by or in contact with humans. These composites are described in U.S. Pat. Nos. 5,360,609, 5,650,466, 5,707, 739, 5,631,300, 5,668,185, and 5,705,902.

Wellinghoff et al. U.S. patent application Ser. No. 08/924, 684 discloses a composite formulated for maximum chlorine dioxide release in which the hydrophilic material contains an α-amino ether and a chlorite salt formed by reaction of an iminium chlorite and a base. Iminium chlorite is unstable to nucleophilic attack by the chlorite anion. When the iminium chlorite is reacted with a base, however, the more stable α-amino ether and chlorite salt are formed.

Wellinghoff et al. U.S. Pat. No. 5,639,295 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or dissolves in the amine to provide chlorite anions. The composite is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite.

Barenberg et al. U.S. patent application Ser. No. 08/724, 907 describes numerous methods of using composites such as those disclosed by Wellinghoff et al. to retard bacterial, fungal, and viral contamination and growth of molds on food, produce, meat, and other materials and to deodorize carpeting and the like.

Although the Wellinghoff et al. composites are effective biocides, there is a need for biocidal compositions in which the acid releasing component and the chlorite containing component form an optically transparent or translucent, single-phase mixture.

SUMMARY OF THE INVENTION

Among the objects of the invention, therefore, may be noted the provision of an optically transparent or translucent composition that releases a concentration of chlorine dioxide sufficient to eliminate bacteria, fungi, molds and viruses; the provision of such a composition that releases such chlorine dioxide concentrations after activation for a period of up to several months; the provision of such a composition that increases the release rate of chlorine dioxide in proportion to increased temperature and humidity which promote mold and bacteria growth; the provision of such a composition that only releases substances approved for human exposure or ingestion; and the provision of an inexpensive composition that does not adversely affect the appearance or mechanical properties of a substrate to which it is applied.

The present invention is directed to a composition for retarding bacterial, fungal and viral contamination and mold growth containing an acid releasing polymer, a hydrophilic material and chlorite anions as components. Each component of the composition has a particle size of not more than about 1,000 angstroms, and is substantially free of water and capable of releasing chlorine dioxide upon hydrolysis of the acid releasing polymer.

Another embodiment of the present invention is directed to a composition for retarding bacterial, fungal and viral contamination and mold growth comprising an amide, chlorite anions, and an acid releasing terpolymer formed from polyvinylpyrrolidone, lactic acid and glycolic acid. Each component of the composition has a particle size of not more than about 1,000 angstroms, and is substantially free of water and capable of releasing chlorine dioxide upon hydrolysis of the acid releasing polymer.

Another embodiment of the invention is directed to a terpolymer having the formula:

wherein PVNP has the formula:

and R is a lower alkyl group or a lower alkyl ester, n is from 5 to 500, x is from 1 to 5,000, y is from 0 to 5,000, and z is from 0 to 5,000, provided that either y or z must be at least one.

Another embodiment of the invention is directed to a multilayered composite for providing sustained release of chlorine dioxide. The composite contains a water-soluble layer comprising an acid releasing polymer, a hydrophilic material and chlorite anions, an upper moisture regulating layer in contact with an upper surface of the water-soluble layer, and a lower moisture regulating layer in contact with a lower surface of the water-soluble layer. The water-soluble layer is substantially free of water and each component of the layer has a particle size of not more than about 1,000 angstroms. The moisture regulating layers are water insoluble, such that moisture permeating either of the moisture regulating layers hydrolyzes the acid releasing polymer to initiate release of chlorine dioxide from the multilayered composite.

Yet another embodiment of the invention is directed to a process for preparing a composition by mixing a hydrophilic material, a chlorite salt, an acid releasing polymer and an organic solvent to form a mixture in which each component has a particle size of not more than about 1,000 angstroms, the mixture being substantially free of water and capable of releasing chlorine dioxide upon hydrolysis of the acid releasing polymer.

Another embodiment of the invention is directed to a process of preparing an acid releasing polymer by mixing a polyvinylpyrrolidone oligomer, lactic acid, glycolic acid and water, and heating the mixture in the presence of an esterification catalyst to form a polyvinylpyrrolidone-lactic acid-glycolic acid terpolymer having acid end groups. The terpolymer is dissolved in an organic solvent, and neutralized to esterify acid end groups of the terpolymer to form the acid releasing polymer.

Another embodiment of the invention is a method of retarding bacterial, fungal, and viral contamination and growth of molds on a surface and/or deodorizing the surface by treating a surface of a substrate with a composition that does not release chlorine dioxide in the absence of moisture, and exposing the treated surface to moisture to release chlorine dioxide from the composition into the atmosphere surrounding the surface. Each component of the composition has a particle size of not more than about 1,000 angstroms.

Yet another embodiment of the invention is a method of retarding bacterial, fungal, and viral contamination and growth of molds on a surface of a material and/or deodorizing the material by exposing a surface of a material to a composition that does not release chlorine dioxide in the absence of moisture, and exposing the composition to moisture to release chlorine dioxide from the composition into the atmosphere surrounding the material. Each component of the composition has a particle size of not more than about 1,000 angstroms.

Yet another embodiment of the invention is a method of retarding bacterial, fungal, and viral contamination and growth of molds on a material and/or deodorizing the material by incorporating a composition that does not release chlorine dioxide in the absence of moisture in a material, and exposing the material to moisture to release chlorine dioxide from the composition into the atmosphere surrounding the material. Each component of the composition has a particle size of not more than about 1,000 angstroms.

Other objects and advantages of the invention will be apparent from the following detailed description.

DETAILED DESCRIPTION OF THE PREFERRED EMBODIMENTS

In accordance with the present invention, it has been discovered that sustained release of chlorine dioxide can be generated from a solution containing chlorite anions when the solution is exposed to moisture. Although chlorine dioxide releasing compositions are known, this solution is unique because it is optically transparent or translucent and is essentially unnoticeable when applied to a substrate. When the solution has been applied to a substrate, the substrate can clearly be seen through the film formed on the substrate. If the solution, for example, is coated onto a containerboard box printed with graphics, the graphics remain clearly visible through the coating. Although the coating releases chlorine dioxide oxidant, the coating does not alter the graphics or effect the color of the graphics. The solution can also be coated on a surface of a transparent or translucent substrate to provide biocidal action while maintaining the "see-through" quality of the substrate. If the solution is coated onto a clear plastic food container, for example, a consumer can see the food within the container before purchasing the food. The biocidal solution protects the food from microbial contamination while allowing consumers to inspect the food without opening the container. The solution, therefore, allows visual inspection of a material while releasing chlorine dioxide to sterilize, deodorize, or protect the material from contamination or infestation.

For purposes of the present invention, a solution is a mixture of components that each have a particle size of not more than about 1,000 angstroms, preferably not more than about 500 angstroms, and more preferably not more than about 100 angstroms as measured by microscopy or light scattering methods that are well known in the polymer art. A solution of the present invention can also be a mixture comprising components that each have a particle size of not more than 2,000 angstroms when the index of refraction of each component of the mixture is the same or substantially similar. A solution including components having any of the above particle sizes is optically transparent or translucent in appearance and visually appears to be a single-phase mixture because its phase microstructure is of a diameter well below the wavelength of visible light. A solution is optically transparent for purposes of the invention when at least about 80% of light, preferably at least about 90%, is transmitted through the solution. The solution does not scatter light and is stable to crystallization that would produce particles larger than 1000 angstroms. The particle size of the solution is preferably small enough for the components to be uniformly dispersed.

Chlorine dioxide is released from the composition when an acid releasing polymer within the composition is hydrolyzed by adsorbed moisture, and releases acid and hydronium ions. The hydronium ions diffuse from the polymer to react with the chlorite anions in the composition to release chlorine dioxide gas. The chlorine dioxide gas diffuses out of the composition into the surrounding atmosphere for a period of up to about six months in order to prevent the growth of bacteria, molds, fungi and viruses on a material. The single-phase compositions provide more complete conversion to chlorine dioxide than is provided by two-phase compositions because the acid releasing polymer and chlorite anions are in a closer proximity to each other than in a two-phase composite. Compositions that release at least about $1.0 \times 10^{-6}$ mole chlorine dioxide/cm$^2$ for a period of at least one week, one month or six months can be formulated by the processes of the present invention for a variety of end uses.

Preferably, the composition comprises between about 0.1 wt. % and about 20 wt. % of chlorite anions and counterions, between about 10 wt. % and about 70 wt. % of a hydrophilic material, and between about 1.0 wt. % and about 50 wt. % acid releasing polymer, more preferably between about 10 wt. % and about 20 wt. % chlorite anions and counterions, between about 10 wt. % and about 50 wt. % hydrophilic material, and between about 10 wt. % and about 30 wt. % acid releasing polymer.

Any acid releasing polymer that forms a solution with the chlorite anions and counterions and the hydrophilic material and is capable of being hydrolyzed by ambient moisture is acceptable for purposes of the present invention. Preferably, the acid releasing polymer does not exude or extract into the environment. The acid releasing polymer preferably has a number average degree of polymerization of between about 10 and about 10,000, more preferably between about 50 and about 1000, and most preferably between about 100 and about 300.

The acid releasing polymer is preferably copolymerized with a hydrophilic oligomer to compatibilize the acid releasing polymer with the chlorite anions and the hydrophilic material. A preferred acid releasing polymer is a copolymer of a phase compatibilizing oligomer such as polyvinylpyrrolidone, polyvinyl alcohol, polyanhydride, or polyacrylamide, and an acid such as lactic acid, glycolic acid, or other α-hydroxy acids or mixtures of these acids. Preferred polyanhydrides have the formula:

wherein R is:

m is 1 or 2, n is an integer from 4 to 12, and X is O or N—CH$_3$.

A particularly preferred acid releasing polymer is a terpolymer of polyvinylpyrrolidone, lactic acid and glycolic acid. Each of the lactic acid, glycolic acid and polyvinylpyrrolidone portions of the terpolymer preferably has a number average degree of polymerization of between about 1 and about 5,000, more preferably between about 5 and about 50 and, most preferably, between about 10 and about 30.

The most preferred acid releasing polymer has the formula:

wherein PVNP has the formula:

R is a lower alkyl group or a lower alkyl ester, n is from 5 to 500, x is from 1 to 5,000, y is from 0 to 5,000, and z is from 0 to 5,000, provided that either y or z must be at least one. R is preferably a methyl group, n is preferably 5 to 100, and x, y and z are preferably 1 to 1,000. The optimum proportions of lactic acid, glycolic acid and polyvinylpyrrolidone in the terpolymer are selected based upon the adhesiveness, stiffness, or other properties required for a desired application of the composition. One of ordinary skill in the polymer art would known how to optimize the proportions of lactic acid, glycolic acid and polyvinylpyrrolidone in the copolymer to obtain desired properties in the composition.

Any hydrophilic material that forms a solution with the chlorite anions and counterions and the hydrophobic material is acceptable for purposes of the present invention. The hydrophilic material is preferably an amide, an amine, or a polyhydric alcohol. When the chlorite source is a chlorite salt, the salt dissociates in the hydrophilic material to form chlorite anions and counterions. However if the hydrophilic material is an amine and the chlorite source is chlorine dioxide gas, the chlorine dioxide reacts with the amine to form iminium chlorite in situ, if the oxidation potential of the amine is sufficiently low for the amine to be oxidized.

The composition of the present invention preferably includes an amide as the hydrophilic material to provide adhesive properties to the composition. The amide is preferably selected from the group consisting of urea or oligomeric amides. Urea is most preferred because its high hydrogen bonding density improves the chlorine dioxide uptake and release efficiency of the composition, it dissolves in and plasticizes polyvinylpyrrolidone, it will not react with the acid releasing polymer, and it provides greater tackiness in the composition. The composition can include up to about 30 wt. % amide, preferably between about 5 and about 20 wt. % amide and, more preferably, between about 10 and about 15 wt. % amide.

The chlorite anions generally do not react with the hydrophilic material or the acid releasing polymer, but are surrounded by hydrogen bonds contributed by the nitrogen or hydroxide within the hydrophilic material or acid releasing polymer. Suitable chlorite sources that can be incorporated into the composition of the present invention include alkali metal chlorites such as sodium chlorite or potassium chlorite, alkaline-earth metal chlorites such as calcium chlorite, chlorite salts of a transition metal ion or a protonated primary, secondary, tertiary or quaternary amine or iminium chlorite salts. Many chlorite sources, such as sodium chlorite, are stable at processing temperatures in excess of about 100° C., allowing for processing at relatively high temperatures.

The components of the composition are substantially free of water to avoid significant release of chlorine dioxide prior to use of the composition. For purposes of the present invention, the composition is substantially free of water if the amount of water in the composition does not provide a pathway for transmission of hydronium ions from the acid releasing polymer to the chlorite anions. Generally, the components of the composition can include up to a total of about 1.0 wt. % water without providing such a pathway for transmission of hydronium ions. Preferably, each component contains less than about 0.1 wt. % water, and, more preferably, between about 0.01 wt. % and about 0.1 wt. % water. Insubstantial amounts of water can hydrolyze a portion of the acid releasing polymer to produce acid and hydronium ions within the composition. The hydronium ions, however, do not diffuse to the chlorite anions until enough free water is present for transport of hydronium ions.

A preferred composition of the present invention includes between about 10 wt. % and about 30 wt. % of a polyvinylpyrrolidone-lactic acid-glycolic acid terpolymer, between about 10 wt. % and about 30 wt. % urea, between about 10 wt. % and between about 20 wt. % chlorite anions, and between about 10 wt % and about 30 wt. % polyvinylpyrrolidone homopolymer.

The composition can also include a compatibilizer to compatibilize the acid releasing polymer with the hydrophilic material and chlorite anions within the composition. A compatibilizer is preferably added when the acid releasing polymer does not include a significant hydrophilic oligomer portion to compatibilize the polymer to the remainder of the composition. Preferred compatibilizers include polyvinylpyrrolidone homopolymer, or its copolymers with alkene oligomers. Polyvinylpyrrolidone is a preferred compatibilizer and also serves to increase the mechanical strength of the composition. The polyvinylpyrrolidone preferably has a number average degree of polymerization between about 1 and about 10,000, more preferably between about 100 and about 10,000 and, more preferably between about 300 and about 5,000.

A plasticizer can be added to the composition to soften the acid releasing polymer. The plasticizer is preferably any monomeric or oligomeric amide generally known in the polymer art as a plasticizer, such as succinamide, formamide, N-methyl formamide, and N-methylacetamide, and isopropylacrylamide-acrylamide. Formamide and N-methyl formamide are toxic and would not be preferred in applications involving human contact. If the polymer amine center is sufficiently mobile, the addition of a plasticizer is unnecessary. A glassy polymer can be softened to increase mobility by adding at least about 10 wt. %, preferably between about 10 and about 30 wt. % of a plasticizer to the polymer to lower glass transition temperature below the reaction temperature. Other amides that can be used as plasticizers for the acid releasing polymer of the invention include $H_2NC(O)(CH_2CH_2O)_nCH_2CH_2C(O)NH_2$ wherein n is 1 to 10, $H_2NC(O)(CH_2CH_2O)_nCH((OCH_2CH_2)_mC(O)NH_2)_2$ wherein n is 1 to 5 and m is 1 to 5, and $N(CH_2CH_2O)_nH_2CH_2(O)NH_2)_3$ wherein n is 1 to 10.

A moisture scavenger, such as sodium sulfate, calcium sulfate, silica gel, alumina, zeolites, and calcium chloride can be added to the composition to prevent premature hydrolysis of the acid releasing polymer. Humectants can be added to render the composition more hydrophilic and increase the rate of hydrolysis of the acid releasing polymer. Conventional film forming additives can also be added to the composition as needed. Such additives include crosslinking agents, flame retardants, emulsifiers and compatibilizers. These additives must be hydrophilic and soluble within the composition if the composition is to be optically transparent or translucent.

Preferred amides for use as the hydrophilic material include urea, formamide, acrylamide-isopropylacrylamide, copolymers of formamide and acrylamide-isopropylacrylamide, and copolymers of acrylamide, isopropylacrylamide or N,N-methylene bisacrylamide and a primary amine or a secondary amine. Such amides can be useful vehicles for film casting prior to exposure to chlorine dioxide, which does not react with polymerizable, electron deficient alkenes such as acrylamide.

Suitable amines for use as the hydrophilic material include primary amines, secondary amines, and tertiary amines having pendant hydrogen bonding groups. An amine substituted with electron donating groups that donate electrons to convert chlorine dioxide to chlorite is preferred. Electron withdrawing groups concentrate electron density at such groups such that it is difficult for the chlorine dioxide to extract an electron from the amine. Tertiary amines having non-hydrogen bonding pendant groups that are dissolved in a hydrophilic solvent are also acceptable. Representative amines include: alkanolamines; copolymers of aminoalkanes and alkene bisacrylamides; alkylaminopyridine; alkene diamines; alkylamino cycloalkanes; alkylaminocarboxyamido alkanes dissolved in a diluent; amines having the formula $R_{3-x}NH_x$; $R_1R_2NCH_2CH_2C(O)NH_2$; solubilized $N(CH_2CH_2OH)_{3-x}H_x$, $R_3N(NCH_2CH_2C(O)NH_2)_2$, $(CH_3)_2N(CH_2)_zN(CH_3)_2$, $R_5R_6N(CH_2)_zNHC(O)NH_2$, $N(CH_2CH_2NHC(O)NH_2)_3$, or wherein: R substituents are, independently, —(CH$_2$CH$_2$O)$_y$H, —C(CH$_3$)$_2$(CH$_2$)$_z$OH, —(CH$_2$)$_z$NH(CH$_2$CH$_2$O)$_z$H, —CH(CH$_3$)$_2$, alkyl, cyvloalkyl, benzyl, acrylamide, or pyridyl; R$_1$, R$_2$, R$_5$, and R$_6$ are alkyl; R$_3$ is methyl or ethyl; m is 1–100; n is 2 or 3; x is 0, 1 or 2; y is 1 or 2; and z is 1, 2 or 3. Generally, the above compounds can be solubilized in formamide, isopropylacrylamide-acrylamide or other conventional plasticizers.

Preferred amines include monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, solubilized 1-(N-dipropylamino)-2-carboxyamido ethane or 1-(N-dimethylamino)-2-carboxyamido ethane, a primary amine having the formula R$_1$NH$_2$, a secondary amine having the formula R$_2$R$_3$NH, N(CH$_2$CH$_2$OH)$_3$, solubilized NR$_5$R$_6$R$_7$, (CH$_3$)$_2$NCH$_2$CH$_2$N(CH$_3$)$_2$, R$_8$R$_9$NCH$_2$CH$_2$C(O)NH$_2$, R$_{11}$R$_{12}$N(CH$_2$)$_3$NHC(O)NH$_2$, N(CH$_2$CH$_2$NHC(O)NH$_2$)$_3$, -continued wherein: R$_1$ is —CH$_2$CH$_2$OCH$_2$CH$_2$OH, —C(CH$_3$)$_2$H$_2$OH, —CH$_2$CH$_2$NHCH$_2$CH$_2$OH, —CH(CH$_3$)$_2$, —CH$_2$CH$_2$OH, R$_2$ and R$_3$ are, independently, n-propyl, isopropyl, acrylamide, or —CH$_2$CH$_2$OH; R$_5$ and R$_6$ are methyl; R$_7$ is 4-pyridyl; R$_8$ and R$_9$ are, independently, methyl, n-propyl or isopropyl; R$_{11}$ and R$_{12}$ are, independently, methyl, ethyl, n-propyl or isopropyl; m is an integer from 1 to 100; and n is 2 or 3. Suitable diluents include formamide or acrylamide-isopropyl acrylamide. Oligomeric or polymeric secondary amines converted to acrylamide substituted tertiary amines by Michael reaction with acrylamides are also suitable because the amide group does not react with the acid releasing agent.

Polyhydric compounds, including glycerol, sorbitol, polyvinyl alcohol, and polyhydric alcohols, can be used as the hydrophilic material. However, chlorine dioxide release can occur more rapidly when a hydroxylic compound is incorporated in the composition and can limit the applications for such compositions to rapid chlorine dioxide releasing systems.

The compositions of the present invention are prepared by mixing the hydrophilic material, a chlorite salt, the acid releasing polymer and an organic solvent to form a mixture having a particle size of not more than about 1,000 angstroms. The mixture is substantially free of water and capable of releasing chlorine dioxide upon hydrolysis of the acid releasing polymer.

The acid releasing polymer is prepared by mixing an oligomer, a carboxylic acid and water to form a mixture. The mixture is heated in the presence of an esterification catalyst to form a copolymer having acid end groups. The copolymer is dissolved in an organic solvent and neutralized to esterify the acid end groups to form the acid releasing polymer. A preferred acid releasing terpolymer is formed by mixing a polyvinylpyrrolidone oligomer, lactic acid, glycolic acid and water to form a mixture, heating the mixture in the presence of an esterification catalyst to form a polyvinylpyrrolidone-lactic acid-glycolic acid terpolymer having acid end groups, dissolving the terpolymer in an organic solvent, and neutralizing the terpolymer to esterify acid end groups of the terpolymer to form the acid releasing polymer. The preparation of this terpolymer is described in Example 2.

The esterification catalyst is preferably selected from the group consisting of p-toluene sulfonic acid, or other strong protic acids (i.e., acids that make an aqueous solution having a pH not greater than 1).

An organic solvent is suitable for preparing the compositions of the invention if the chlorite salt is substantially soluble in the organic solvent and the solvent is substantially free of water. The organic solvent is preferably methanol or ethanol, and is most preferably methanol.

A preferred solution includes between about 10 wt. % and about 30 wt. % of a polyvinylpyrrolidone-lactic acid-glycolic acid terpolymer, between about 10 wt. % and about 30 wt. % urea, between about 10 wt. % and between about 30 wt. % chlorite anions, between about 10 wt % and about 30 wt. % polyvinylpyrrolidone homopolymer, and between about 30 wt. % and about 60 wt. % methanol. The methanol in the solution evaporates when the solution is cast as a film or formed into some other end product.

Chlorine dioxide is released, for example, from this preferred composition by exposing the composition to moisture. The moisture hydrolyzes the acid releasing terpolymer, forming polyvinylpyrrolidone oligomer, lactic acid and glycolic acid within the composition. The lactic acid and glycolic acid react with water to form hydronium ions. The hydronium ions react with a chlorite salt to form chlorine dioxide and metal salts of lactic or glycolic acid. The hydrolysis is illustrated below:

by the initial electron transfer from the amine is rapidly complexed and stabilized by a hydrophilic molecule. In some formulations, uncomplexed chlorite anion may be depleted by subsequent reactions with the iminium counterion at temperatures above about 60° C. Chlorites are also subject to disproportionation into chloride and chlorate. An amine with a high $pK_a$ is preferred because it reacts more rapidly with chlorine dioxide and acts as a more effective proton sink, maintaining the basic pH required for chlorite ion stability.

Chlorine dioxide is released from iminium chlorite when moisture contacts the composition. Hydrolysis of the acid releasing polymer provides hydronium cations ($H_3O^+$) that react with iminium chlorite to release chlorine dioxide gas. The decomposition products of the reaction are aminium chloride salts and organic carboxylates. These products are retained within the composition.

It has been found that, in some instances, iminium chlorite may decompose if the composition is exposed to temperatures exceeding about 60° C., reducing the available chlorite concentration for conversion to chlorine dioxide. In order to The rate of chlorine dioxide release from a composition can be controlled when preparing the composition by changing the viscosity of the composition, changing the concentration of acid releasing polymer in the composition, changing the crystallinity of the components in the composition, and by adding a desiccant or humectant to the composition to control release of chlorine dioxide from the composition once it is exposed to moisture. The rate of chlorine dioxide release can be controlled during use by changing the temperature or moisture content of the composition.

The compositions of the present invention that contain an amine can form iminium chlorite rather than dissolved chlorite anions. Iminium chlorite is formed when the amine hydrophilic material is in contact with the hydrophobic acid releasing polymer. Chlorine dioxide ($ClO_2$) is reduced by extracting an electron from the amine, forming an aminium radical cation and a chlorite counterion ($ClO_2^-$). The aminium cation quickly converts to an iminium cation by loss of a proton from an adjacent carbon atom and oxidation by another chlorine dioxide molecule. The mechanism for above reaction in an aqueous system is described by Rosenbatt et al., J. Org. Chem., 28, 2790 (1963); J. Amer. Chem. Soc. 89(5), 1158, 1163 (1967).

High chlorine dioxide to chlorite conversions are obtained if the chlorite anion and/or iminium cation that is generated maximize chlorine dioxide release from the composite, it has been discovered that the chlorite source can be omitted from the composition until the composition is applied to a surface when the hydrophilic material in the composition is an amine. After application, the composition is exposed to chlorine dioxide gas that either reacts with the amine to form iminium chlorite in situ or dissolves in the amine to provide chlorite anions. The composition is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite. Chlorine dioxide can be provided on site by passing the composition through a chlorine dioxide generator.

In order for an amine to form iminium chlorite in neat form or in the presence of a plasticizer, the amine must be sufficiently electron rich and the amine nitrogen must be locally mobile. Electron withdrawing groups should be separated from the amine center by at least two methylene groups in order for the chlorine dioxide to extract an electron from the amine. Movement of the bonds about the nitrogen center of the amine is required for aminium formation. If the amine is frozen into a glassy matrix, the amine nitrogen will not be mobile and the amine will not convert to iminium chlorite. A glassy amine can be softened to increase mobility by adding at least about 10 wt. % of a plasticizer, such as a low molecular weight amide, to the amine to lower glass transition temperature below the reaction temperature. Other suitable plasticizers are well known in the polymer art.

Maximum chlorine dioxide release from a composition can be achieved by stabilizing the chlorite anion. Iminium chlorite is unstable to nucleophilic attack by the chlorite anion. It has been discovered that the room temperature lifetime of chlorite anion is substantially extended when a strong base, such as a metal alkoxide, is present in the hydrophilic material containing the iminium chlorite. The mechanism of alkoxide stabilization of the chlorite counterion is shown below.

wherein $R'_2$ and $R_2$ are groups that correspond to those of the selected amine and R" is an alkyl or hydrogen group. In the absence of water, the iminium ion is immediately decomposed into an α-amino ether and a more stable sodium chlorite salt. If water is present during the oxidation of the tertiary amine, an unstable α-amino alcohol is formed that can attack the chlorite anion unless the chlorite anion has been effectively complexed by the hydrophilic solvent. Addition of water after salvation of the chlorite ion is not as deleterious.

Acceptable strong bases for use in stabilizing the chlorite include metal alkoxides such as sodium, potassium or calcium methoxides, ethoxides, propoxides or butoxides, metal oxides such as aluminum oxide, or sodium oxide, metal ions such as $Na^+$, trialkyl ammonium salts of alkoxides, ammonium salts of alkoxides, acetates such as sodium acetate, substituted acetates, or other materials that would generate a strong basic reaction to attack the nitrogen center of iminium chlorite.

The compositions of the present invention can be formulated in various ways to accommodate a wide range of end use applications. The composition can be formulated as an extrudate, such as a film or pellets, or as a powder using conventional extrusion and spray drying methods, respectively.

The composition of the invention can be formulated as a powder. Although the powder is not optically transparent, it provides a slow rate of release of a low concentration of chlorine dioxide as compared to chlorite particles coated with a hydrophobic material. To prepare the powder, anhydrous particles are fed into a fluidized bed. A solution of the acid releasing polymer, the hydrophilic material and chlorite anions in an organic solvent as described above is aerosolized by passing the material through small diameter nozzles into the chamber of the fluidized bed where it can impinge upon the fluidized anhydrous particles. Upon contact with the fluidized particles, the chlorine dioxide releasing powder is formed as the solution solidifies to form an acid releasing core having a layer of anhydrous particles embedded in the outer surface thereof. Aggregation is minimized because the anhydrous particles are hard inorganic materials. The particles can then be packaged in a dry sealed container.

In forming the chlorine dioxide releasing powder, the anhydrous particles delay release of chlorine dioxide that is catalyzed by atmospheric moisture. Suitable anhydrous materials include anhydrous sodium sulfate, calcium sulfate, magnesium sulfate, and a moisture depleted silica gel. Additional anhydrous particles can also be post-mixed with the chlorine dioxide releasing powder to delay chlorine dioxide release.

In addition to formation of powdered composites, the composition of the present invention can be formulated in solvents to allow for film casting or other application methods. The composition can be applied as a film by using well known hot melt, dip coat, spray coat, curtain coat, dry wax, wet wax, coextrusion and lamination processes.

Figure 1:
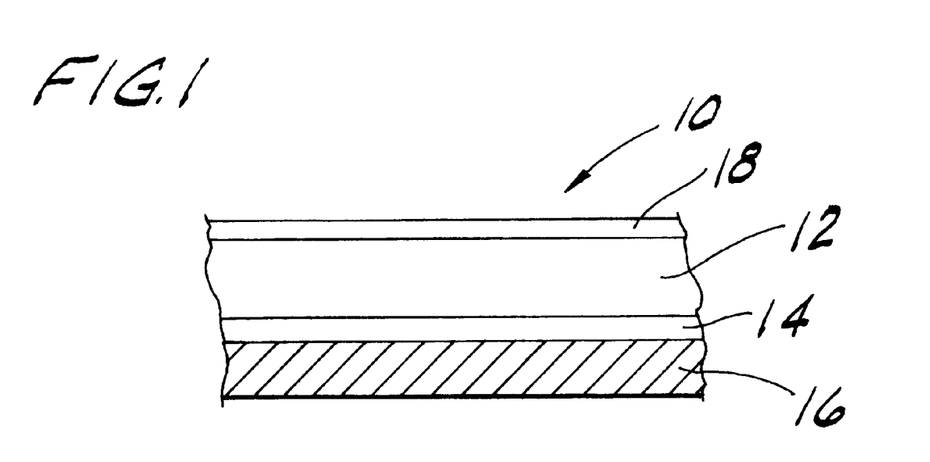
FIG. 1 is a schematic of a multilayered composite for providing sustained release of chlorine dioxide.

The compositions can also be used in forming a multilayered composite 10 including a water-soluble, optically transparent or translucent layer 12 comprising an acid releasing polymer, chlorite anions, and a hydrophilic material as shown in FIG. 1. The water-soluble layer 12 is cast onto a moisture regulating layer 14 on a substrate 16, and a moisture regulating layer 18 is then cast onto the water-soluble layer 12. The moisture regulating layers 14 and 18 are water-insoluble, water-permeable films, that prevent the water-soluble layer 12 from degrading in the presence of moisture. This arrangement enables a chlorine dioxide atmosphere to be provided over a period of days, weeks or months. The moisture regulating layers also control the rate of moisture ingress into the water-soluble layer to control chlorine dioxide release from the multilayered composite when activated by moisture. Suitable water-insoluble, water-permeable films can be composed of poly(ethylene-propylene) or poly(acrylic-ester acrylate) copolymers or ionomers thereof such as sulfonated salts of poly(ethylene-propylene). Hydroxyethylmethacrylate, methoxyethylmethacrylate, copolymers of at least one hydrophilic component and at least one hydrophobic component, and other water-insoluble, water-permeable films well known in the art are also suitable.

The layered composites of the present invention are intended to maintain a desired rate of chlorine dioxide release (moles/sec/$cm^2$ of film) in the presence of atmospheric moisture at a surface for a length of time required for chlorine dioxide to absorb onto the surface and kill bacteria or other microbiological contaminants. However, leakage from a container or exposed surface reduces the chlorine dioxide concentrations at the surface because of chlorine dioxide diffusion into the atmosphere. The chlorine dioxide concentration released from the film for a chosen time period can be calculated given the leakage rate and the rate of absorbance at a surface. Thus after measuring the leakage rate, the composite is formulated so that it contains a large enough reservoir of chlorite reacting at a speed sufficient to compensate for the leakage rate for the desired time period of sustained release.

Therefore, design of a chlorine dioxide releasing composite suitable for controlled release and biocidal action within a container must take into account several aspects, namely, the chlorine dioxide production rate from the controlled release film, the partitioning of chlorine dioxide between the phases within the container (e.g. gas, liquid and solid phases) in a reversible (absorbed) or irreversible (reacted) fashion, and the leakage rate of gas from the container. Design of such a composite is described in Example 15 of U.S. Pat. No. 5,705,092.

A preferred extended release system of the present invention conserves the chlorite reservoir by emitting a series of periodic pulsed releases timed to coincide with the suspected times of bacterial, viral or fungal contamination or the typical incubation time for the biological of interest. The system design can be optimized to maintain the desired kill concentration for the requisite time at the atmospheric chlorine dioxide leakage rates imposed by the specific application.

A typical controlled release multilayered composite includes water-soluble layers A that are each formed from a composition of the invention. The layers typically have a thickness of about 5 mil, and are separated from each other by a water-swellable intermediate layer C.

The intermediate layer C can be composed of a wide variety of materials since chlorine dioxide can diffuse equally well in both hydrophobic and hydrogen bonded matrices. Such optically transparent or translucent materials include copolymers of at least one hydrophilic monomer or oligomer and at least one hydrophobic monomer or oligomer, polyionomers such as protonated and neutralized, sulfonated, or phosphorylated oligo- or poly-alkenes such as polyethylene, polypropylene, alkyl acrylates, hydroxyethylmethacrylate, methoxyethylmethacrylate and copolymers thereof. Lipid substituted polyhydroxy alcohol phosphates and phosphosilicates and their mixtures with alkene polymers and oligomers can be used but will not form an optically transparent composite. Finely divided anhydrous salts or desiccants may be added to any of the layers to retard the reaction to chlorine dioxide that is catalyzed by water.

It has been discovered that construction of a multilayered composite wherein the arrangement of the layers in the composite is defined by the formula $C(ACA)_nC$ (wherein n represents the desired number of pulses) provides periodic pulsed release of high concentrations of chlorine dioxide over several weeks or months. Such pulsed release can be coordinated to the growth, incubation and contamination of viruses, molds, fungi and bacteria. The cycle time and peak concentrations of chlorine dioxide would be controlled by the layer thickness, chlorite and acid releasing polymer loading, and the water and ionic permeation characteristics of layers A and C. Pulsed release occurs as each layer $(ACA)_I$ is successively penetrated by water vapor and hydronium ions.

Pulsed releases of chlorine dioxide that vary from about one day to over about 200 days can be achieved for 5 mil thick A and C films by separating the A layers by an intermediate layer C capable of supporting varying hydronium ion transport rates.

The pulsed release capabilities of a multiple layered film can be calculated as provided in Example 16 of U.S. Pat. No. 5,705,092.

Applications for the compositions of the invention are numerous. The water-soluble compositions can be used in most any environment where exposure to moisture will occur so long as the compositions are protected from degradation by a water-insoluble, water-permeable material or are incorporated as a component of a material. The compositions can be used to prevent the growth of molds, fungi, viruses and bacteria on the surface of a material, deodorize the material or inhibit infestation by treating a surface of a substrate with a composition that does not release chlorine dioxide in the absence of moisture, and exposing the treated surface to moisture to release chlorine dioxide from the composition into the atmosphere surrounding the surface. The release of chlorine dioxide retards bacterial, fungal, and viral contamination and growth of molds on the surface, deodorizes the surface, and inhibits infestation. Each component of the composition has a particle size of not more than about 1,000 angstroms.

The surface can be treated with a composition of the present invention by conventional coating, extrusion, lamination and impregnation methods well known in the art. The treated surface is generally a portion of a container, a part of a substrate placed within a container, or a packaging film or other type of packaging. When an optically transparent composition of the invention has been applied to a substrate, the substrate surface can clearly be seen through the film formed on the surface. If the composition, for example, is coated onto a containerboard box printed with graphics, the graphics remain clearly visible. A container or substrate can be protected with a coating of the biocidal composition although the composition is transparent and virtually unnoticeable to a consumer.

The biocidal atmosphere generated within the container or other packaging can be used in storing food products including blueberries, raspberries, strawberries, and other produce, ground beef patties, chicken filets, and other meats, enhanced foods, pet foods, dry foods, cereals, grains, or most any food subject to bacterial contamination or mold growth. Bar soap, laundry detergent, stored paper documents, clothing, paint, seeds, footwear, and packaging therefor can also be protected from mold growth, mildew, fungus and algae. Medical instruments, devices and supplies, disposable or nondisposable personal care products, and soil can be sterilized to prevent microbial contamination. Medical, biological or biohazardous waste in hospitals, laboratories, and clinics can also be sterilized to kill microbials within the waste. Odors from athletic shoes, disposable footwear, and refuse can also be minimized when they are contained within a treated container.

Electronic or photographic equipment and supplies, such as VCRs, video tapes, audio tapes, audio components, cameras, photographic film, camera lenses, lenses within medical equipment, and medical monitors and other medical equipment, can also be treated with the composition or exposed to the composition to prevent growth of mold, moldew, fungus and algae. The biocidal composition can be incorporated into a polymer melt used to make a portion of the equipment and supplies, such as the video tape cartridge or equipment housing. The cartridge or housing can also include a film of the composition adhered to the interior thereof. The biocidal composition can replace silica gel packs typically used in shipment and storage of electronic and photographic equipment.

The compositions of the invention are especially suitable for application to or incorporation in transparent or translucent products. The compositions can also be coated on a surface of a transparent or translucent substrate to provide biocidal action while maintaining the "see-through" quality of the substrate. If the solution is coated onto a clear plastic food container, for example, a consumer can see the food within the container before purchasing the food. The biocidal solution protects the food from microbial contamination while allowing consumers to inspect the food without opening the container. The solution, therefore, allows visual inspection of a material while releasing chlorine dioxide to sterilize, deodorize, or protect the material from contamination or infestation. When the compositions are applied to clear surgical bandages, the wound is sterilized by the chlorine dioxide and is visible through the bandage, allowing for inspection of the wound without removing the bandage and exposing the wound to contamination.

Transparent or translucent products that can be treated with the compositions of the invention include clear packaging such as "clam-shell" containers, clear packaging films such as plastic wrap for food, disposable eating utensils, plates and cups, food serving products, food wrappings, containers for food storage, and other food packaging, portable water filters for treating water during camping, boating, trips or emergencies, waste containers or bags for medical or biohazardous waste. Packaging can be treated with the composition to preserve food products having a long-term shelf life, such as "fresh" shelf-stable processed foods kept at room temperature including soft tortillas, cakes or other baked goods, energy bars, candy, snack foods, and the like. Clear biodegradable and non-degrading sutures for use in humans and animals can be treated to prevent infection at the site of use, maintain sterility of the sutures during storage, and to sterilize the sutures for use as an alternative to steam, ethylene oxide, and gamma irradiation. Clear "see-through" bandages, band-aids and surgical dressings can also be treated with the multilayered composites described above to reduce microbial contamination and infection.

The compositions of the invention are also especially suited for providing a clear, invisible coating on products such as furniture and floors used in settings prone to microbial contamination such as hospitals. The compositions can also be incorporated or coated onto filters and ducts for heating, ventilation and air conditioning to prevent microbial contamination, alleviate "sick building syndrome," and prevent the outbreak of Legionnaires' disease resulting from *Legionella premophilia* bacterium.

Conventional containers can be used such as paperboard or containerboard boxes, corrugated, nonwoven, plastic, foamed or polymeric-multilaminate containers, "clamshell"0 containers commonly used in the fast food industry, cellulosic, plastic or paper bags, seed packets, or waste containers.

The treated surface can also be a reusable or disposable mat or sheet including a dental tray covering, a surgical tray covering, a shower mat, nonwoven bandage material, a meat cutting board, a liner for drawers or shelves, an insert for athletic bags or gym lockers, a food wrapper, a paper sheet for separating hamburger patties, a meat packaging tray, an overpouch such as those used in packaging intravenous bags, a fresh fruit separator or box liner, an absorbent pad for poultry, meat, seafood or produce, or an absorbent layer for use in diapers. Such mats or sheets are typically made from paper, cellulosic, polymeric, woven fabric or nonwoven materials.

Such a method can also be used to coat the surface of a seed to protect the seed from molds and fungi during storage and to protect against mycotic growth when the seed is planted. The coating, when activated by moisture, creates a microatmosphere of chlorine dioxide in the soil in the vicinity of the seed and inhibits mycotic growth that normally would impede seed germination. This coating has no effect upon the germination of the seeds. Seeds in storage do not have to be physically coated to be protected but rather can be in a closed container containing the active material as a packet, "tea bag" or coating on the container. Paper impregnated with the composite generates sufficient chlorine dioxide to protect the seeds. Although any seeds can be protected by the coating, edible seeds such as corn kernels, sunflower seeds, or soybeans, remain fit for human consumption once they are coated. Thus, the coated seeds can be provided for planting or for human consumption after they have been coated. An optically transparent composition of the invention can be applied to the seeds to ensure that the appearance of the seeds will not be altered by the composition.

Another embodiment of the invention is a method of preventing the growth of fungi, bacteria or molds on a surface and/or deodorizing the surface by treating the surface with a composition that does not release chlorine dioxide in the absence of moisture, and exposing the treated surface to moisture to release chlorine dioxide from the composition into the atmosphere surrounding the surface.

A preferred application includes a foot powder for preventing athlete's foot and other fungi. The powder can be applied directly on the surface of the foot or can be incorporated into a shoe insert. The powder can be applied between the cloth covering and foam pad of the shoe insert, impregnated within the foamed pad, or impregnated or coated on a shoe counter or upper lining. Chlorine dioxide generated from moisture within the shoe diffuses from the composite into the atmosphere to kill fungus and deodorize the shoe. The powder can be blended with conventional ingredients such as talc, cornstarch, fragrance, miconazole nitrate, tolnastate silica, boric acid, aluminum chlorhydrate, salicylic acid, and cellulose. The powder can also be blended with other ingredients and used in bath powders or powders used in treating jock itch.

The powder can also be applied to carpeting to remove odors from the carpet. Ingredients commonly incorporated in powdered carpet deodorizers or cleaners can be blended with the powder of the present invention. The composite can also be formulated in microcapsules that break after being stepped on and are then activated by moisture. Such microcapsules can be impregnated in floor, shower or bath mats or can be used in carpet deodorization. The powders can also be packaged in a sachet and placed in marine environments, such as the deck, sump or storage areas on boats, to prevent mildew and mold growth in these areas.

Another use for the compositions is in providing self sterilizing packaging, which is particularly useful in the medical industry. The composition can be coated onto tubing, connectors, fitments or other components. Fitments for in-dwelling catheters, needles, peritoneal dialysis, percutaneous devices, percutaneous access, intravenous bags, colostomy bags and other medical devices can also be treated in accordance with this method to sterilize the devices and to prevent insertion site infections, sinus track infections, and the like. Additionally, closures on a package can be so treated to provide self sterilizing packaging for medical devices, instruments and supplies.

The composition of the present invention was expected to kill bacteria on the surface of meats. However, it was not expected to penetrate a ground beef patty. It has been discovered that chlorine dioxide evolved from paper treated with the composition can effectively penetrate the full thickness of a patty and kill bacteria such as *E. coli* and Salmonella that result from contamination during meat processing. *E. coli* 0157:H7 in tainted meat has caused death and severe illness and appears to be especially resistant to cooking, fermenting and drying. In a typical operation producing meat patties for commercial consumption, meat is ground, extruded and formed into patties that are separated by sheets of coated paper that prevent adhesion of the individual patties. After packaging, the ground meat can be exposed to chlorine dioxide over a period of time when in refrigerated storage to kill and inhibit the growth of the bacteria.

The following examples are presented to describe preferred embodiments and utilities of the present invention and are not meant to limit the present invention unless otherwise stated in the claims appended hereto.

EXAMPLE 1

A polyvinylpyrrolidone oligomer was prepared by polymerizing vinyl pyrrolidinone in water using a free radical initiation with hydrogen peroxide and ammonia catalyst as described by E. S. Barabas, Encyl. Poly. Sci. Eng., 17, 198 (1989). Three grams of vinyl pyrrolidinone were dissolved in seven grams of water and polymerized with 0.03 ml of 30% hydrogen peroxide and 0.3 ml concentrated ammonium water for five hours at 55° C. The reaction products were polyvinylpyrrolidone oligomer and 2-pyrrolidone. At the end of the reaction an additional two ml of 30% hydrogen peroxide was added to oxidize any terminal aldehyde groups to carboxylic acid groups. After solvent was pumped off and the product was vacuum dried at 60° C., a clear, hard polyvinylpyrrolidone oligomer terminated by hydroxyl and carboxyl groups was recovered. The reaction is illustrated below:

wherein PVNP represents polyvinylpyrrolidone, which has the formula:

wherein n=5 to 500.

EXAMPLE 2

A multiblock, polyester copolymer of polyvinylpyrrolidone was prepared by mixing 0.46 g of the polyvinylpyrrolidone oligomer prepared in Example 1, 0.23 g glycolic acid and 0.225 ml of 85% lactic acid with 1.5 ml water and 0.005 g p-toluene sulfonic acid esterification catalyst. The mixture was slowly heated over 20 hours to 120° C. under dynamic vacuum to remove the water of esterification. A multiblock terpolymer having acid end groups was recovered. To esterify the acid end groups, the copolymer was dissolved in a large excess of methanol and neutralized with ammonia. Alternatively, the acid end groups can be esterified with excess methanol. End groups —OR— rather than the CH$_3$O— end group shown in the reaction scheme below—can be formed by dissolving the polymer in an excess of an alcohol or by dissolving the polymer in an alcohol and neutralizing with ammonia. The alcohol has the formula ROH wherein R is ethyl, n-propyl, or isopropyl. The resultant polyvinylpyrrolidone-polylactate-glycolate (PVNP-PLGA) terpolymer contained 34 mole % polyvinylpyrrolidone, 32 mole % glycolate and 24 mole % lactate. The preparation of the PVNP-PLGA terpolymer is shown below:

EXAMPLE 3

A 30 wt. % solution of the PVNP-PLGA terpolymer prepared according to Example 2 in methanol was neutralized with triethylamine and added to a methanol solution (10 wt. % total solids) of sodium chlorite (recrystallized from methanol), urea and polyvinylpyrrolidone (360,000 MW) so that the total solids mixture contained 51 wt. % PVNP-PLGA terpolymer, 34 wt. % polyvinylpyrrolidone homopolymer, 9 wt. % urea and 6 wt. % sodium chlorite. The solution was cast into a film and remained uniformly dispersed and transparent indefinitely.

EXAMPLE 4

A solution of the PLGA copolymer in chloroform was added to a methanol solution (10 wt. % total solids) of sodium chlorite (recrystallized from methanol), urea (10 wt. % total solids) and polyvinylpyrrolidone (360,000 MW). The solution remained cloudy and separated into a PLGA phase and a polyvinylpyrrolidone-urea-chlorite phase when cast into a film.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A composition for retarding bacterial, fungal and viral contamination and mold growth comprising an acid releasing polymer, a hydrophilic material, and chlorite anions, each component of the composition having a particle size of not more than about 1,000 angstroms, and the composition being substantially free of water and capable of releasing chlorine dioxide upon hydrolysis of the acid releasing polymer.

2. The composition of claim 1 wherein the composition is optically transparent.

3. The composition of claim 1 wherein the composition is a single phase.

4. The composition of claim 1 wherein the composition is a film.

5. The composition of claim 1 wherein the hydrophilic material is an amide, an amine or a polyhydric alcohol.

6. The composition of claim 5 wherein the amide is urea or an oligomeric amide.

7. The composition of claim 6 wherein the composition includes polyvinylpyrrolidone.

8. The composition of claim 7 wherein the polyvinylpyrrolidone has a number average degree of polymerization of between about 1 and about 10,000.

9. The composition of claim 6 wherein the composition includes a hydrophilic or oligomeric plasticizer selected from the group consisting of succinamide, formamide, N-methyl formamide, N-methylacetamide, and isopropylacrylamide-acrylamide.

10. The composition of claim 5 wherein the chlorite anions are provided by an iminium chlorite or a chlorite salt selected from the group consisting of alkali metal chlorites, alkaline earth metal chlorites, and chlorite salts of a transition metal ion, or a protonated primary, secondary, tertiary or quaternary amine.

11. The composition of claim 1 wherein the acid releasing polymer has a number average degree of polymerization of between about 10 and about 10,000.

12. The composition of claim 11 wherein the acid releasing polymer is a copolymer formed from polyvinylpyrrolidone, polyvinyl alcohol, polyanhydride, or polyacrylamide and at least one α-hydroxy acid.

13. The composition of claim 12 wherein the copolymer is formed from polyvinylpyrrolidone, lactic acid and glycolic acid.

14. The composition of claim 13 wherein each of the lactic acid, glycolic acid and polyvinylpyrrolidone portions of the copolymer preferably has a number average degree of polymerization of between about 1 and about 5,000.

15. The composition of claim 14 wherein the copolymer has the formula:

wherein PVNP has the formula:

and R is a lower alkyl group or a lower alkyl ester, n is from 5 to 500, x is from 1 to 5,000, y is from 0 to 5,000, and z is from 0 to 5,000, provided that either y or z must be at least one.

16. The composition of claim 1 wherein at least about $1.0 \times 10^{-6}$ mole chlorine dioxide/cm$^2$ is released from the composition for a period of at least one week after initial exposure to moisture.

17. The composition of claim 1 wherein at least about $1.0 \times 10^{-6}$ mole chlorine dioxide/cm$^2$ is released from the composition for a period of at least one month after initial exposure to moisture.

18. The composition of claim 1 wherein at least about $1.0 \times 10^{-6}$ mole chlorine dioxide/cm$^2$ is released from the composition for a period of at least six months after initial exposure to moisture.

19. A composition for retarding bacterial, fungal and viral contamination and mold growth comprising an amide, chlorite anions, and an acid releasing terpolymer formed from polyvinylpyrrolidone, lactic acid and glycolic acid, each component of the composition having a particle size of not more than about 1,000 angstroms, and the composition being substantially free of water and capable of releasing chlorine dioxide upon hydrolysis of the acid releasing polymer.

20. The composition of claim 19 wherein the composition is optically transparent.

21. The composition of claim 19 wherein the composition is a film.

22. The composition of claim 19 wherein the amide is urea or an oligomeric amide.

23. The composition of claim 19 wherein the composition includes polyvinylpyrrolidone.

24. The composition of claim 23 wherein the polyvinylpyrrolidone has a number average degree of polymerization of between about 1 and about 10,000.

25. The composition of claim 19 wherein the chlorite anions are provided by an iminium chlorite or a chlorite salt selected from the group consisting of alkali metal chlorites, alkaline earth metal chlorites, and chlorite salts of a transition metal ion, or a protonated primary, secondary, tertiary or quaternary amine.

26. The composition of claim 19 wherein the acid releasing terpolymer has a number average degree of polymerization of between about 10 and about 10,000.

27. The composition of claim 26 wherein the acid releasing terpolymer is formed from polyvinylpyrrolidone, polyvinyl alcohol, polyanhydride, or polyacrylamide and at least one α-hydroxy acid.

28. The composition of claim 27 wherein the terpolymer has the formula:

wherein PVNP has the formula:

and R is a lower alkyl group or a lower alkyl ester, n is from 5 to 500, x is from 1 to 5,000, y is from 0 to 5,000, and z is from 0 to 5,000, provided that either y or z must be at least one.

29. The composition of claim 19 wherein at least about $1.0\times10^{-6}$ mole chlorine dioxide/cm$^2$ is released from the composition for a period of at least one week after initial exposure to moisture.

30. The composition of claim 19 wherein at least about $1.0\times10^{-6}$ mole chlorine dioxide/cm$^2$ is released from the composition for a period of at least one month after initial exposure to moisture.

31. The composition of claim 19 wherein at least about $1.0\times10^{-6}$ mole chlorine dioxide/cm$^2$ is released from the composition for a period of at least six months after initial exposure to moisture.

32. A multilayered composite for providing sustained release of chlorine dioxide comprising:
a water-soluble layer comprising an acid releasing polymer, a hydrophilic material and chlorite anions, the layer being substantially free of water and each component of the layer having a particle size of not more than about 1,000 angstroms; and
an upper moisture regulating layer in contact with an upper surface of the water-soluble layer, and a lower moisture regulating layer in contact with a lower surface of the water-soluble layer, the moisture regulating layers being water insoluble, such that moisture permeating either of the moisture regulating layers hydrolyzes the acid releasing polymer to initiate release of chlorine dioxide from the multilayered composite.

33. A multilayered composite for providing time pulsed release of chlorine dioxide comprising:
at least two water-soluble layers comprising an acid releasing polymer, a hydrophilic material and chlorite anions, the layers being substantially free of water and each component of the layers having a particle size of not more than about 1,000 angstroms; and
at least three water-insoluble, water-permeable barrier layers to control the diffusion of water or the diffusion of hydronium ions produced by hydrolysis of the acid releasing polymer into the water-soluble layer;
the arrangement of the layers in the composite being defined by the formula C(ACA)$_n$C wherein C is a barrier layer, A is a water-soluble layer, and n is an integer ranging from 1 to 10.

34. A process for preparing a composition comprising:
mixing a hydrophilic material, a chlorite salt, an acid releasing polymer and an organic solvent to form a mixture in which each component has a particle size of not more than about 1,000 angstroms, the mixture being substantially free of water and capable of releasing chlorine dioxide upon hydrolysis of the acid releasing polymer.

35. The process of claim 34 further including the step of preparing the acid releasing polymer by mixing a polyvinylpyrrolidone oligomer, lactic acid, glycolic acid and water; heating the mixture in the presence of an esterification catalyst to form a polyvinylpyrrolidonelactic acid-glycolic acid terpolymer having acid end groups; dissolving the terpolymer in an organic solvent; and neutralizing the terpolymer to esterify acid end groups of the terpolymer to form the acid releasing polymer.

36. The process of claim 35 wherein the esterification catalyst is p-toluene sulfonic acid.

37. The process of claim 35 wherein the organic solvent is selected from the group consisting of methanol and ethanol.

38. The process of claim 34 further including the step of applying the composition to a substrate to form a film.

39. The process of claim 38 further including the step of exposing the film to moisture to hydrolyze the acid releasing polymer and release chlorine dioxide from the composition.

40. The process of claim 38 wherein the composition is applied as a tacky hot melt at a temperature below that at which chlorite within the composition will decompose.

41. The process of claim 38 wherein at least about $1.0\times10^{-6}$ mole chlorine dioxide/cm$^2$ is released from the film for a period of one week after initial exposure to moisture.

42. The process of claim 38 wherein at least about $1.0\times10^{-6}$ mole chlorine dioxide/cm$^2$ is released from the film for a period of one month after initial exposure to moisture.

43. The process of claim 38 wherein at least about $1.0\times10^{-6}$ mole chlorine dioxide/cm$^2$ is released from the film for a period of six months after initial exposure to moisture.

44. A process for preparing a composition comprising:
mixing an amine and an acid releasing polymer to form a mixture; and
exposing the mixture to chlorine dioxide that reacts with the amine to form iminium chlorite within the mixture, the mixture having a particle size of not more than about 1,000 angstroms and being capable of releasing chlorine dioxide upon hydrolysis of the acid releasing polymer.

45. The process of claim 44 wherein the mixture includes a base and, when exposed to chlorine dioxide, the chlorine dioxide reacts with the amine to form iminium chlorite which is decomposed by the base to form a chlorite salt within the mixture.

46. The process of claim 44 wherein the chlorine dioxide dissolves within the amine to form chlorite anions in the mixture.

47. A method of retarding bacterial, fungal, and viral contamination and growth of molds on a surface and/or deodorizing the surface comprising:
treating a surface of a substrate with the composition of claim 1 or 19; and
exposing the treated surface to moisture to release chlorine dioxide from the composition into the atmosphere surrounding the surface to retard bacterial, fungal, and viral contamination and growth of molds on the surface and/or deodorize the surface.

48. The method of claim 47 wherein the substrate is flooring, furniture, a seed, biodegradable sutures, non-degrading sutures, a bandage, a surgical dressing, an in-dwelling catheter, a disposable eating utensil, plate or cup, a food serving product, a food wrapping, a container for food storage, packaging, a portable water filter, a waste container or bag for medical or biohazardous waste, a filter for heating, ventilation and air conditioning, soil, footwear, or photographic or electronic equipment or supplies.

49. The method of claim 47 wherein the composition is optically transparent.

50. The method of claim 47 wherein the composition is comprised of an acid releasing polymer, a hydrophilic material, and chlorite anions.

51. A method of retarding bacterial, fungal, and viral contamination and growth of molds on a surface of a material and/or deodorizing the material comprising:

exposing a surface of a material to the composition of claim 1 or 19; and exposing the composition to moisture to release chlorine dioxide from the composition into the atmosphere surrounding the material to retard bacterial, fungal, and viral contamination and growth of molds on the surface of the material and/or deodorize the material.

52. The method of claim 50 wherein the material is a seed, meat, poultry, seafood, fresh foods, or processed foods, a disposable eating utensil, plate or cup, soil, footwear, or photographic or electronic equipment or supplies.

53. The method of claim 52 wherein the meat, poultry or seafood is a ground patty or a filet, and bacterial, fungal, and viral contamination and growth of molds is reduced on the surface and throughout the patty or filet.

54. The method of claim 52 wherein the composition is a packaging film.

55. The method of claim 50 wherein the composition is optically transparent.

56. The method of claim 50 wherein the composition is comprised of an acid releasing polymer and chlorite anions.

57. A method of retarding bacterial, fungal, and viral contamination and growth of molds on a material and/or deodorizing the material comprising:

incorporating the composition of claim 1 or 19 in a material;

exposing the material to moisture to release chlorine dioxide from the composition into the atmosphere surrounding the material to retard bacterial, fungal, and viral contamination and growth of molds on the material and/or deodorize the material.

58. The method of claim 57 wherein the material is biodegradable sutures, non-degrading sutures, a bandage, a surgical dressing, an in-dwelling catheter, a disposable eating utensil, plate or cup, a food serving product, a food wrapping, a container for food storage, packaging, a portable water filter, a waste container or bag for medical or biohazardous waste, a filter for heating, ventilation and air conditioning, soil, footwear, or photographic or electronic equipment or supplies.

59. The method of claim 57 wherein the composition is comprised of an acid releasing polymer and chlorite anions.

* * * * *

UNITED STATES PATENT AND TRADEMARK OFFICE
CERTIFICATE OF CORRECTION

PATENT NO. : 5,922,776
DATED : July 13, 1999
INVENTOR(S) : Stephen T. Wellinghoff et al.

It is certified that error appears in the above-identified patent and that said Letters Patent is hereby corrected as shown below:

<u>Title page,</u>
Under the title of the Assignee, it incorrectly reads:

"Bernard Technologies, Inc., Chicago, Ill." which should correctly read
--- Bernard Technologies, Inc., Chicago, IL; and Southwest Research Institute, San Antonio, TX ---.

Signed and Sealed this

Fourteenth Day of August, 2001

*Attest:*

*Attesting Officer*

NICHOLAS P. GODICI
*Acting Director of the United States Patent and Trademark Office*